(12) United States Patent
Marcotte et al.

(10) Patent No.: US 10,987,051 B2
(45) Date of Patent: Apr. 27, 2021

(54) SURGICAL INSTRUMENT WITH NERVE DETECTION FEATURE

(71) Applicant: Ethicon LLC, Guaynabo, PR (US)

(72) Inventors: Amy L. Marcotte, Mason, OH (US); Timothy G. Dietz, Reading, MA (US); Donna L. Korvick, San Antonio, TX (US); Ashvani K. Madan, Mason, OH (US); William D. Dannaher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 226 days.

(21) Appl. No.: 15/899,720

(22) Filed: Feb. 20, 2018

(65) Prior Publication Data

US 2018/0242910 A1 Aug. 30, 2018

Related U.S. Application Data

(63) Continuation of application No. 13/442,020, filed on Apr. 9, 2012, now abandoned.

(51) Int. Cl.
*A61B 5/00* (2006.01)
*A61B 17/32* (2006.01)
(Continued)

(52) U.S. Cl.
CPC ........ *A61B 5/4893* (2013.01); *A61B 18/1445* (2013.01); *A61B 2017/00026* (2013.01); *A61B 2017/00106* (2013.01); *A61B 2017/320093* (2017.08); *A61B 2017/320094* (2017.08); *A61B 2017/320095* (2017.08); *A61B 2017/320097* (2017.08); *A61B 2018/00791* (2013.01)

(58) Field of Classification Search
CPC .............................. A61N 7/00; A61H 23/0245
See application file for complete search history.

(56) References Cited

U.S. PATENT DOCUMENTS 5,980,510 A 11/1999 Tsonton et al.
6,500,176 B1 12/2002 Truckai et al.
(Continued)

FOREIGN PATENT DOCUMENTS

CN 2043120 U 8/1989
CN 1041873 A 5/1990
(Continued)

OTHER PUBLICATIONS

U.S. Appl. No. 13/442,020 (US Pat. Pub. No. 2013/0267874).
(Continued)

*Primary Examiner* — Hien N Nguyen
(74) *Attorney, Agent, or Firm* — Frost Brown Todd LLC (57) ABSTRACT

A surgical apparatus comprises an instrument body, an end effector, and a control module. The end effector is in communication with the handle assembly. The end effector is operable for use in a surgical procedure. The control module is in communication with the end effector. The end effector with the control module is able to deliver surgical energy as well as nerve excitation energy to a surgical site. A surgeon may detect stimulation of nervous tissue by visually observing the tissue twitch, and may adjust surgical technique accordingly. A sensor may be used to detect excitation of nervous tissue based on excitation caused by the nerve excitation energy.

15 Claims, 6 Drawing Sheets

(51) Int. Cl.
*A61B 18/14* (2006.01)
*A61B 18/00* (2006.01)
*A61B 17/00* (2006.01)

(56) References Cited

U.S. PATENT DOCUMENTS

| | | |
|---|---|---|
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,416,101 B2 | 8/2008 | Shelton, IV et al. |
| 7,738,971 B2 | 6/2010 | Swayze et al. |
| 8,063,770 B2 | 11/2011 | Costantino |
| 8,753,333 B2 | 6/2014 | Johnson et al. |
| 2002/0120188 A1 | 8/2002 | Brock et al. |
| 2004/0034340 A1 | 2/2004 | Biscup |
| 2004/0204734 A1 | 10/2004 | Wagner et al. |
| 2006/0079874 A1 | 4/2006 | Faller et al. |
| 2007/0100334 A1 | 5/2007 | McFarlin |
| 2007/0191713 A1 | 8/2007 | Eichmann et al. |
| 2007/0282333 A1 | 12/2007 | Fortson et al. |
| 2008/0039915 A1 | 2/2008 | Van Den Biggelaar |
| 2008/0146921 A1 | 6/2008 | Novak et al. |
| 2008/0200940 A1 | 8/2008 | Eichmann et al. |
| 2009/0033486 A1 | 2/2009 | Costantino |
| 2009/0143797 A1 | 6/2009 | Smith et al. |
| 2009/0209979 A1 | 8/2009 | Yates et al. |
| 2009/0209990 A1 | 8/2009 | Yates et al. |
| 2010/0069940 A1 | 3/2010 | Miller et al. |
| 2011/0015660 A1 | 1/2011 | Wiener et al. |
| 2011/0087212 A1 | 4/2011 | Aldridge et al. |
| 2011/0087218 A1 | 4/2011 | Boudreaux et al. |
| 2011/0160731 A1 | 6/2011 | Bleich et al. |
| 2012/0210223 A1 | 8/2012 | Eppolito |
| 2012/0253372 A1* | 10/2012 | Ross .............. A61B 17/320092 606/169 |
| 2013/0267874 A1 | 10/2013 | Marcotte et al. |

FOREIGN PATENT DOCUMENTS

| | | |
|---|---|---|
| DE | 102010017117 A1 | 12/2011 |
| JP | S63-019134 A | 1/1988 |
| JP | H07-194608 A | 8/1995 |
| JP | 2003-126112 A | 5/2003 |
| JP | 2008-000611 A | 1/2008 |
| JP | 2008-503255 A | 2/2008 |
| JP | 2010-088898 A | 4/2010 |
| JP | 2011-517596 A | 6/2011 |
| WO | WO 2005/074831 A2 | 8/2005 |
| WO | WO 2011/008672 A2 | 1/2011 |
| WO | WO 2011/015586 A1 | 2/2011 |
| WO | WO 2011/136962 A2 | 11/2011 |
| WO | WO 2011/147971 A1 | 12/2011 |

OTHER PUBLICATIONS

Australian Patent Examination Report No. 1, dated Nov. 24, 2016 for Application No. AU 2013246284, 3 pages.
Chinese First Office Action dated Mar. 25, 2016 for Application No. CN 201380018833.4, 12 pages.
International Preliminary Report on Patentability and Written Opinion dated Oct. 14, 2014 for Application No. PCT/US2013/035060.
International Search Report and Written Opinion dated Jun. 19, 2013 for International Application No. PCT/US2013/035060.
Japanese Notification of Reasons for Refusal dated Dec. 13, 2016 for Application No. JP 2015-505791, 4 pages.
U.S. Appl. No. 61/410,603, filed Nov. 5, 2010.
Brazilian Office Action dated Dec. 23, 2019 for Application No. BR 112014025194-0, 4 pgs.
Canadian Office Action dated Mar. 4, 2019 for Application No. CA 2,869,749, 3 pgs.
Canadian Office Action dated Nov. 18, 2019 for Application No. CA 2,869,749, 3 pgs.
Chinese Search Report dated Mar. 7, 2016 for Application No. CN 201380018833.4, 2 pgs.
Chinese Office Action dated Jan. 16, 2017 for Application No. CN 201380018833.4.
Indian Office Action dated Jun. 23, 2020 for Application No. 7890/DELNP/2014, 7 pgs.
Japanese Search Report by Registered Search Organization dated Dec. 7, 2016 for Application No. JP 2015-505791, 45 pgs.
Japanese Office Action, Decision to Grant a Patent, dated May 9, 2017 for Application No. JP 2015-505791, 2 pgs.

* cited by examiner

SURGICAL INSTRUMENT WITH NERVE DETECTION FEATURE

This application is a continuation application of U.S. Non-provisional application Ser. No. 13/442,020, filed Apr. 9, 2012, entitled "Surgical Instrument with Nerve Detection Feature," published as U.S. Pat. Pub. No. 2013/0267874 on Oct. 10, 2013, now abandoned.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While a variety of surgical instruments have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Surgical Instrument

Figure 1:
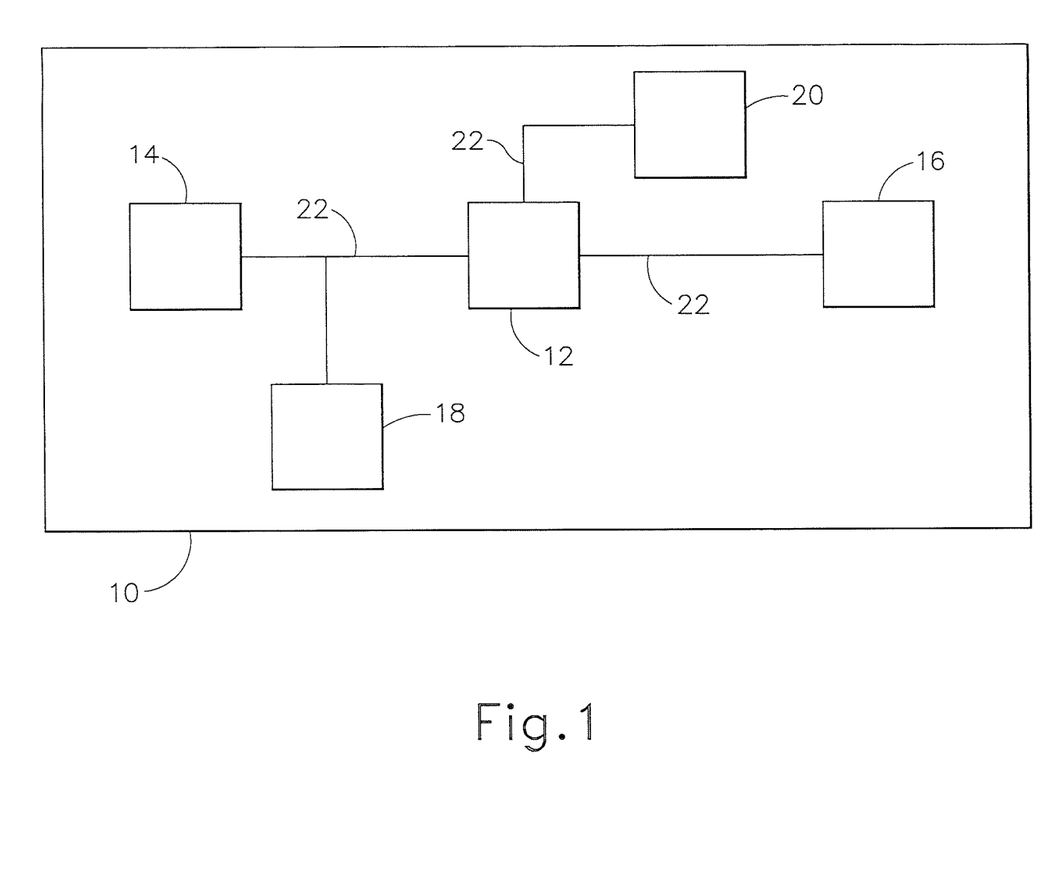
FIG. 1 depicts a block diagram view of an exemplary surgical instrument.

FIG. 1 shows components of an exemplary medical device and/or surgical instrument (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse. In addition or in the alternative, control module (12) may be removed for servicing, testing, replacement, or any other purpose as will be apparent to one of ordinary skill in the art in view of the teachings herein. Control module (12) may also be operable to provide pulsing energy through use of power source (14) as will be discussed further below.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired. Further detail regarding sensor (20) and variations thereof will be discussed below.

II. Exemplary Ultrasonic Surgical Instrument

Figure 2:
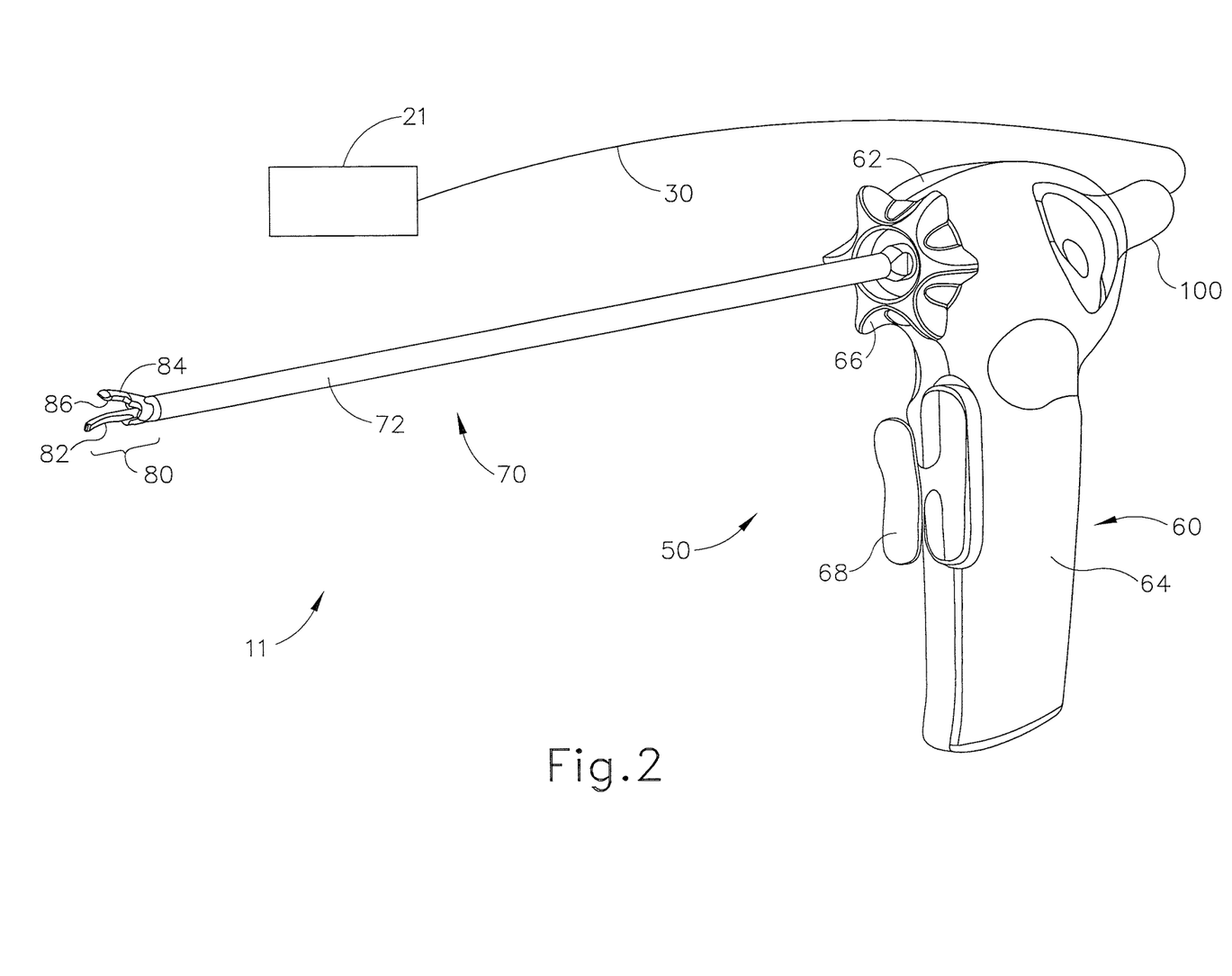
FIG. 2 depicts a perspective view of an exemplary ultrasonic surgical instrument.

FIG. 2 shows a surgical system (11), which includes an exemplary ultrasonic version (50) of instrument (10) described above. When ultrasonic components of instrument (50) are inactive, tissue can be readily gripped and manipulated, as desired, without tissue cutting. When the ultrasonic components are activated, instrument (50) permits tissue to be gripped by end effector (80) for coupling with the ultrasonic energy to effect tissue coagulation, with application of increased pressure efficiently effecting tissue cutting and coagulation. If desired, ultrasonic energy can be applied to tissue without use of the clamping mechanism of end effector (80) by appropriate manipulation of the ultrasonic blade (82).

By way of example only, surgical system (11) may be constructed and/or operable in accordance with any suitable teachings or combinations of teachings from any of the following: U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744, on Jun. 11, 2013, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Exemplary ultrasonic surgical system (11) comprises an ultrasonic surgical instrument (50), a generator (21), and a cable (30) operable to couple generator (21) to surgical instrument (50). A suitable generator (21) is the GEN 300 sold by Ethicon Endo-Surgery, Inc. of Cincinnati, Ohio. By way of example only, generator (21) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, issued as U.S. Pat. Pub. No. 2009/0143797, issued as U.S. Pat. No. 8,419,757 on Apr. 16, 2013. Furthermore, surgical device (50) may also be used, or adapted for use, in robotic-assisted surgery settings such as that disclosed in U.S. Pat. No. 6,783,524.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, now abandoned and U.S. Pat. Pub. No. 2008/0200940, now abandoned. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. It should also be understood that some versions of end effector (80) may lack clamp arm (84). For instance, end effector (80) may simply include blade (82). The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, issued as U.S. Pat. No. 8,461,744 on Jun. 11, 2013. Toggle buttons (not shown) may be located on a distal surface of lower portion (64) and may be operable to activate transducer (100) at different operational levels using generator (21). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein.

Still other suitable forms that system (11) and components thereof may take will be apparent to those of ordinary skill in the art in view of the teachings herein.

III. Surgical Instrument with Nerve Detection Features

It will be appreciated that in some instances, it may be desirable to either avoid or simply have knowledge of when a surgical instrument, such as instruments (10, 50) described above, is near nervous tissue. In other instances, it may be desirable for a user to interact with nervous tissue. For example, during the surgical procedure, the user may wish to ablate a portion of nervous tissue or use information measured from nervous tissue to determine the whether the nervous tissue is experiencing excessive heat, etc. Intentional nerve ablation may be performed in a procedure on a patient's epicardium to reduce the incidence of arrhythmia, in procedures setting a nerve block to manage chronic pain, in aesthetic procedures to able wrinkle creating nerves, etc. Other information related to or arising from nervous tissue may be used or otherwise desirable, as will be apparent to one of ordinary skill in the art in view of the teachings herein.

Figure 3:
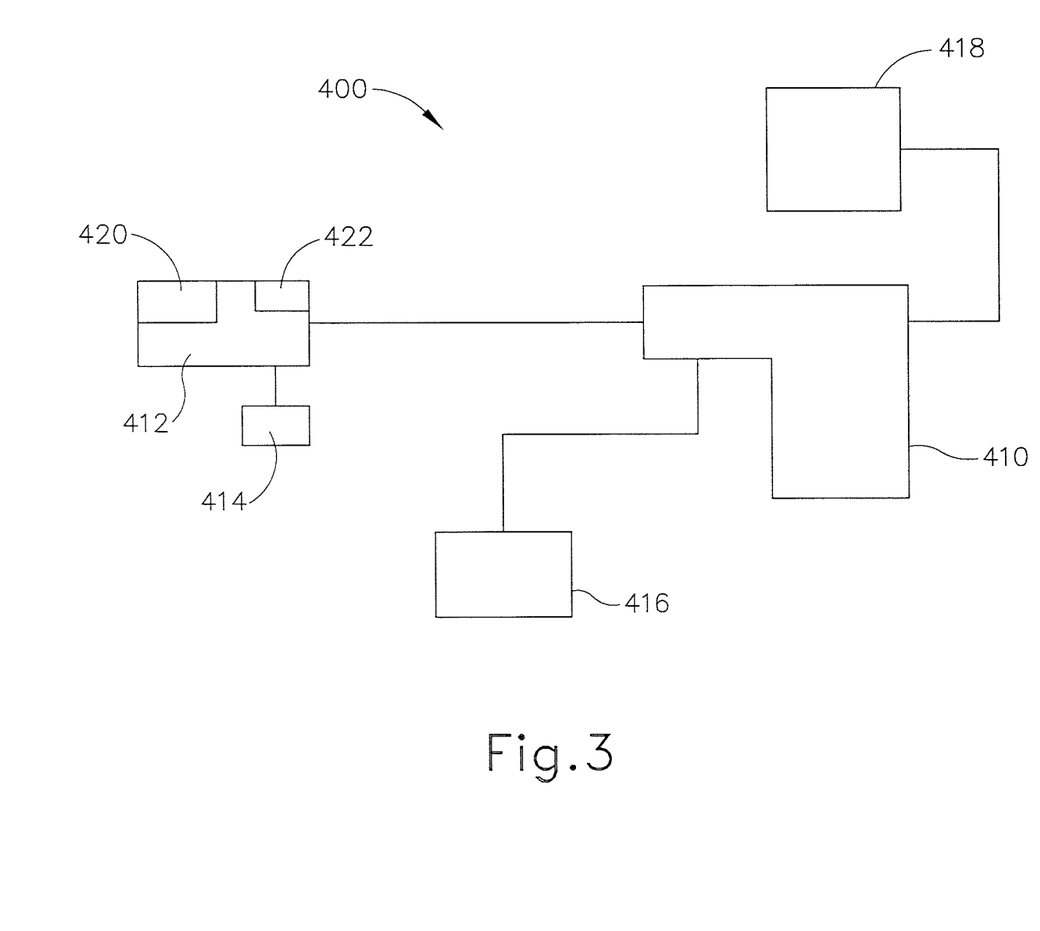
FIG. 3 depicts a block diagram view of an exemplary surgical instrument with a sensor.

FIG. 3 shows one exemplary version of a surgical instrument (400) having an end effector (412) attached to a handle assembly (410). Handle assembly (410) is in communication with a power source and/or generator (418). Handle assembly (410) is also in communication with a control board (416), which, in the exemplary version, is operable to control many of the functions related to detecting whether end effector (412) is near nervous tissue. Surgical instrument (400) of this example may be viewed as a variation of instruments (10, 50) described above. It will be appreciated that while the exemplary version shows one layout/configuration, other potential layouts and configurations are contemplated. For example, while control board (416) is depicted as being located outside of handle assembly (410), other suitable locations for control board (416) may be used as would be apparent to one of ordinary skill in the art in view of the teachings herein. As an alternative example, control board (416) may be integrated into handle assembly (410), into end effector (412), into power source (418), and/or elsewhere. Similarly, it will be appreciated that power source (418) may have different configurations than the exemplary version shown in FIG. 3. For example, power source (418) may be located outside of handle assembly (410); or be contained within or integrated with handle assembly (410). In yet other exemplary versions, power source (418), end effector (412), and control board (416) may be integrated together. Other suitable configurations will be apparent to one of ordinary skill in the art in view of the teachings herein.

A. Exemplary Nerve Stimulus

There are numerous ways to detect the presence or proximity of nervous tissue, particularly by stimulating nerves and detecting responses. For instance, nervous tissue may be stimulated by applying direct or proximate pressure on the nerve, which may cause the nerve to generate an electrical signal that can be either observed visually by a muscular twitch or monitored electrically by detecting evoked response potentials. Nervous tissue may also be stimulated by applying direct or proximate electrical current, which can be modulated to increase or decrease the response of the nerve. Higher currents may result in increased response, but may also tend to degrade the ability to localize the stimulated nerve more accurately. Bipolar electrical stimulation may overcome this by creating localized field currents and placing location identification within the confines of the applied field. Electrical stimulation may be provided through a single surface electrode, multiple surface electrodes, inserted electrodes, interoperative probes or needles used in the surgical field during surgery, and/or in numerous other ways. Heat may also be used to stimulate nervous tissue, since nervous tissue may provide a detectable response to heat. For instance, heat may be applied using a probe, focused electromagnetic energy such as a microwave, laser, or focused ultrasound. As yet another merely illustrative example, focused high intensity magnetic field gradients may be used to stimulate nerves, which may enable detection of such nerves. Various examples of how the above-described nerve stimulation/detection techniques may be incorporated into a surgical instrument (such as instruments (10, 50) described above, etc.) will be described in greater detail below; while others will be apparent to those of ordinary skill in the art in view of the teachings herein.

In the present example, power source (418) is in communication with end effector (412) such that power source (418) can provide AC and/or DC current to tissue through end effector (412) to thereby stimulate the tissue, which may in some cases include the stimulation of nervous tissue. In some versions (e.g., versions where direct current is provided through an ultrasonic blade at end effector (412), etc.), a conventional surgical ground pad may be placed under the patient to facilitate the flow of DC electrical current by providing a return path. By way of example only, this may be readily implemented in versions of instrument (400) where end effector (412) includes an ultrasonic blade but no clamping member (e.g., as taught in U.S. Pat. Pub. No. 2008/0200940, now abandoned, etc.), versions of instrument (400) where end effector (412) includes a clamping member and is configured for use in open procedures (e.g., as taught in U.S. Pat. Pub. No. 2007/0191713, now abandoned and/or U.S. Pat. Pub. No. 2007/0282333, now abandoned, etc.), and versions of instrument (400) where end effector (412) includes a clamping member and is configured for use in laparoscopic procedures (e.g., as taught in U.S. Pat. Pub. No. 2006/0079874, now abandoned, etc.). Other suitable types of instruments that may incorporate the above teachings will be apparent to those of ordinary skill in the art in view of the teachings herein.

As another merely illustrative example, a ground pad may be omitted and a clamping member (e.g., clamp pad (86), etc.) at end effector (412) may provide a return path for the nerve stimulus current. By way of example only, such functionality may be readily incorporated into versions of instrument (400) where end effector (412) includes a clamping member and is configured for use in open procedures (e.g., as taught in U.S. Pat. Pub. No. 2007/0191713, now abandoned and/or U.S. Pat. Pub. No. 2007/0282333, now abandoned, etc.) and versions of instrument (400) where end effector (412) includes a clamping member and is configured for use in laparoscopic procedures (e.g., as taught in U.S. Pat. Pub. No. 2006/0079874, now abandoned, etc.). Other suitable types of instruments that may incorporate the above teachings will be apparent to those of ordinary skill in the art in view of the teachings herein. It should also be understood that a ground pad may still be used under the patient even in instances where a clamping member at end effector (412) provides an electrical return path.

As yet another merely illustrative example, instead of delivering a nerve stimulus current through an ultrasonic blade at end effector (412), a clamping member (e.g., clamp pad (86), etc.) at end effector (412) may be used to deliver a nerve stimulus current to tissue. In some such versions, a conventional surgical ground pad may be placed under the patient to facilitate the flow of DC electrical current by providing a return path. As a variation of this, an ultrasonic blade at end effector (412) may be used to provide a return path for the nerve stimulus current, in addition to or in lieu of using a ground pad under the patient to provide a return path for the nerve stimulus current. As still another merely illustrative variation, a clamping member (e.g., clamp pad (86), etc.) at end effector (412) may include a pair of nerve stimulus electrodes that are used to provide a nerve stimulus current to tissue. Such electrodes may be spaced apart from each other laterally and/or longitudinally, with a dielectric coating and/or other insulator positioned between the electrodes. Other configurations for providing nerve stimulus current through end effector (412) will be apparent to those of ordinary skill in the art in view of the teachings herein.

As an alternative to regular AC or DC current, pulsatile current may be provided through end effector (412). By way of example only, a suitable pulsatile current may have a pulse width of approximately 0.05 to 5 milliseconds, a pulse repetition rate of approximately 0.2 to 100 Hz, and amplitude between approximately 0.1 and 10 mA with a corresponding impedance range of less than approximately 500 ohms to 10 kohms. It will be understood that these parameters may be independently adjusted, based on a variety and/or combination of factors including but not limited to the following: the amplitude of the evoked response from the nervous tissue, the threshold amount of current to be applied to cause an evoked response from the nervous tissue, the latency between the stimulus and the evoked response, the thickness of the nervous fibers that may be stimulated, etc. The amplitude of evoked response may depend on factors such as the number of nerve fibers that are stimulated (e.g., the larger the nerve bundle and/or the deeper the penetration of the stimulating current, the greater the measured amplitude of evoked response, etc.). It should be understood that once the applied current exceeds the threshold amount required to cause an evoked response from the nervous tissue, further increases in current may depolarize an increasing region of tissue and may thus suppress the response time o the tissue to subsequent stimulus. It should also be understood that the latency between the stimulus and the evoked response may be increased if the stimulating current saturates the nerve; and that the latency may be indicative of the local environment around the nerve (e.g., skeletonization may increase latency and/or the length of nerve fiber traveled from the point of firing to the point of measurement.

Of rouse, power source (418) may be operable to provide a variety of different types and combinations of types of nerve stimulus in a surgical procedure.

B. Exemplary Nerve Stimulus Detection

There are numerous ways to monitor responses to nervous tissue stimuli. For instance, a sensor may be used to detect evoked potentials generated by stimulated nerves, including spontaneous nerve activity by sensory and somatic nerves. It should also be understood that nerve stimulation may be monitored through electromyography (EMG). An example of this is described in U.S. Pub. No. 2009/0033486, entitled "System and Method for Facial Nerve Monitoring," published Feb. 5, 2009, issued as U.S. Pat. No. 8,063,770 on Nov. 22, 2011, the disclosure of which is incorporated by reference herein. Of course, another technique may include visual observation of muscle twitching caused by nerve stimulus. As another merely illustrative example, nerve conduction may be monitored. Nerves may have a characteristic response to a periodic stimulation. If the intervening nerves are damaged, then this damage may be evidenced by a change in this characteristic response. Observed changes may include amplitude, rise time, fall time, persistence, latency, etc. As yet another merely illustrative example, motor evoked potentials may be monitored. An example of this is Transcranial Electric Motor Evoked Potential (TCe-MEP), where the motor cortex is stimulated transcranially, and recordings are made from muscles in the limbs, or from the spinal cord caudal to the surgery. Yet another merely illustrative example may include the use of one or more mechanical sensors adjacent tissue to detect twitching or other movement of stimulated nervous tissue. Various examples of how monitoring techniques like those described above may be incorporated into a surgical instrument (such as instruments (10, 50) described above, etc.) will be described in greater detail below; while others will be apparent to those of ordinary skill in the art in view of the teachings herein.

It should be understood that providing an appropriate level of AC current through nervous tissue may cause the tissue to visibly twitch. Such twitching may be visually observable by the surgeon by simply seeing the twitching. It may nevertheless be desirable in some instances (e.g., where visibility of stimulated tissue is obstructed or otherwise limited, etc.) to provide additional sensing of reactions in nervous tissue in response to an electrical current or other form of stimulus. To that end, end effector (412) of surgical instrument (400) comprises a sensor (420), indicator (422), and switch (414). Sensor (420), indicator (422), switch (414), and end effector (412) are in communication with each other. Sensor (420) may comprise any suitable type of sensor. For example, sensor (420) may comprise an electrical impedance sensor/monitor, a vibration sensor, a Doppler fiber operable to sense acoustic changes, a pressure or torque sensor, a heat sensor, one or more electrodes built on/into the surface of end effector (412), or even an electrical wire operable to transmit electrical current that can be measured, which may be operable to detect the presence of nervous tissue. By way of example only, sensor (420) may be configured to sense evoked response potentials generated in nervous tissue in response to a stimulus. Such versions may include one or more electrodes that are amplified to enhance the signal-to-noise ratio associated with sensed evoked response potentials. Sensor (420) may be integrally formed with end effector (412) (e.g., integrated into an ultrasonic blade and/or clamping member, etc.) or may be positioned on the outside of end effector (412) as would be apparent to one of ordinary skill in the art in view of the teachings herein.

As can also be seen in FIG. 3, indicator (422) is in communication with end effector (412). In some versions, indicator (422) may be positioned on or within handle assembly (410) or any other suitable location. In the exemplary version, indicator (422) is operable to inform the user that end effector (412) is near, or is touching, nervous tissue. In particular, sensor (420) detects the nervous tissue and subsequently, control board (416) triggers indicator (422) to tell the user that nervous tissue has been reached. In some versions, indicator (422) may include a selectively illuminated light, a color changing light, a buzzer or other audio sound, or a vibration generator that tactile/haptic a physical feedback for the user through handle assembly (410). It will be appreciated that indicator (422) may take other forms as would be apparent to one of ordinary skill in the art in view of the teachings herein. By way of example only, indicator (422) may be provided as part of power source (418) in addition to or in lieu of being incorporated into end effector (412). In some such versions, power source (418) may also be configured to provide an indication to the surgeon when end effector (412) is in an active state (e.g., when an ultrasonic blade is being activated). Thus, power source (418) may be configured to provide both an indication of when end effector (412) is in an active state and when end effector (412) is near or touching nervous tissue. For instance, power source (418) may provide a continuous audible tone at one octave to indicate activation of end effector (412) and another audible tone at a higher or lower octave to indicate proximity to nervous tissue. As another merely illustrative example, such audible tones may be provided in periodically repetitive pairs. Still other suitable ways in which power source (418) may provide audible feedback simultaneously indicating two (or more) different conditions will be apparent to those of ordinary skill in the art in view of the teachings herein.

In some versions, switch (414) may be incorporated into end effector (412). Switch (414) is operable to selectively activate or deactivate algorithms, routines, programs, executable functions, etc., run by control board (416) for delivering nerve stimulus AC current to end effector (412). Alternatively, switch (414) can be used to selectively activate, deactivate, engage, or disengage any suitable portion of surgical instrument (400). For example, switch (414) may control the activation of sensor (420). In other words, it will be understood that depending on the situation, the user may or may not need to detect the presence of nervous tissue, which can accordingly be controlled via switch (414). While switch (414) is in communication with end effector (412) in the present example, it will be appreciated that switch (414) may be located on handle assembly (410), power source (418), or a module located between power source (418) and handle assembly (410). Other suitable locations for switch (414) will be apparent to one of ordinary skill in the art in view of the teachings herein. Switch (414) may also take a variety of forms such as a toggle switch, a slider switch, one or more buttons, or any other suitable type of switch (414) as would be apparent to one of ordinary skill in the art. It will further be understood that in some instances, switch (414) may be omitted entirely such that sensor (420) and the associated components continually detect nervous tissue.

In yet other variations, it will be appreciated that sensor (420), switch (414), and indicator (422) may be modularly attached to end effector (412) such that they may be moved, or used in conjunction with a different surgical device and/or instrument. Yet in some versions, sensor (420), switch (414), and indicator (422) may be constructed such that they are integrally formed with end effector (412) and/or handle assembly (410) or a shaft extending from handle assembly (410).

C. Exemplary Surgical Instrument with Dual Function Blade and Sensing Clamp Arm

Figure 4:
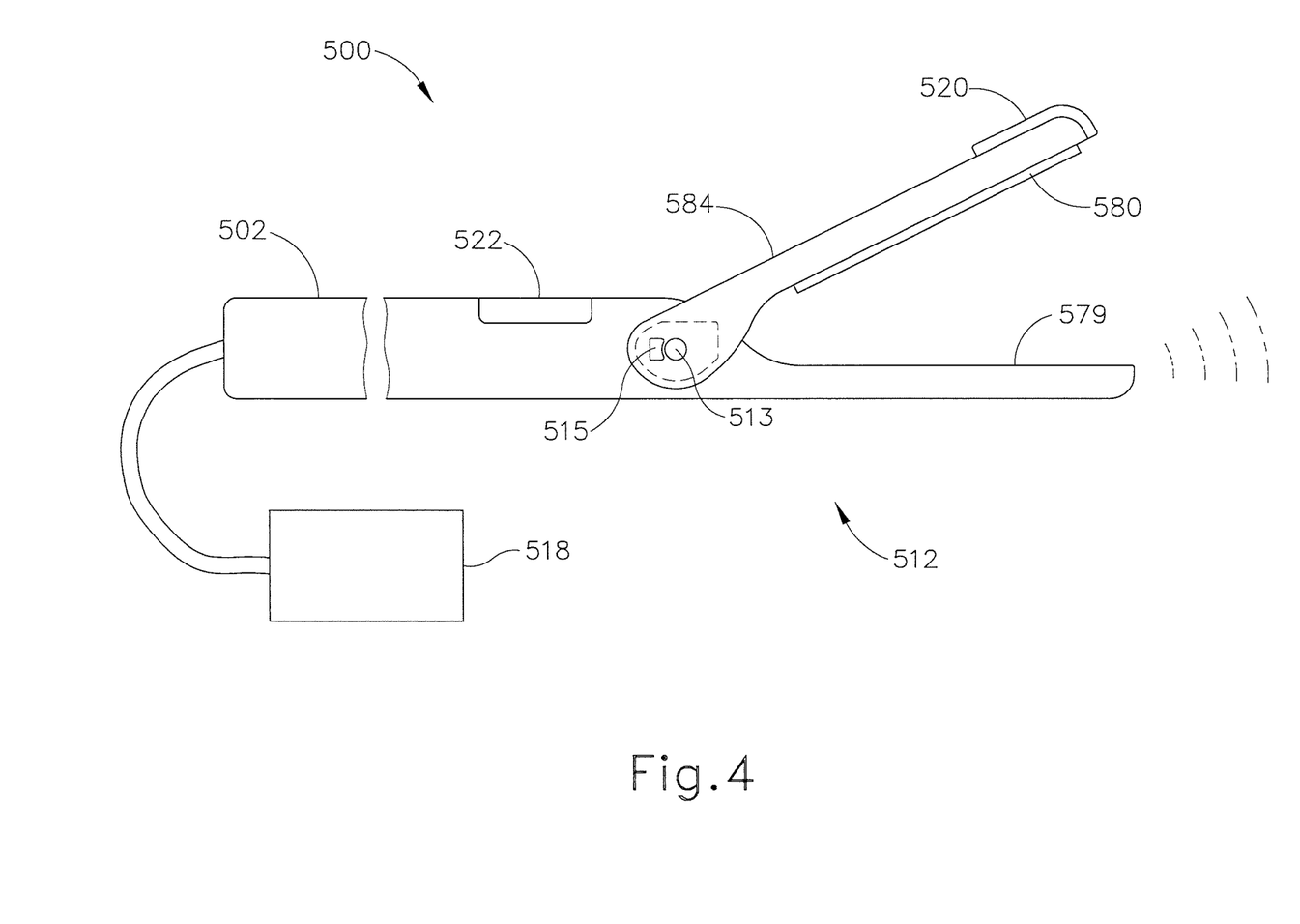
FIG. 4 depicts a side view of an end effector of an exemplary surgical instrument with a sensor in accordance with the block diagram of FIG. 3.

FIG. 4 shows one exemplary version of a surgical instrument (500) having a shaft (502) leading to an end effector (512). End effector (512) comprises a blade (579) and clamp arm (584) operable to clamp tissue to deliver RF energy, ultrasonic vibration energy, or any other suitable type of surgical/therapeutic energy. Power source (518) is operable to drive blade (579) to deliver such surgical/therapeutic energy to tissue. It will be appreciated that in addition to surgical/therapeutic energy used for cutting, cauterizing, etc., blade (579) is operable to deliver electrical energy (e.g., DC/AC/pulsatile current) capable of stimulating nerve cells, fibers, and/or tissue. By delivering such energy, nervous tissue near end effector (512) may become excited, resulting in a variety of actions as described above. For example, nervous tissue may twitch, experience a change in impedance, may experience a change in electrical activity, exhibit an evoked potential or other response, etc. Other perceivable changes to nervous tissue may occur as would be apparent to one of ordinary skill in the art in view of the teachings herein. It should be understood that clamp arm (584) is shown merely as an illustrative example. The teachings herein may be readily applied to variations of end effector (512) that lack a clam arm (584). For instance, the teachings herein may be readily applied to versions of end effector (512) that just have blade (579).

It will be understood that energy delivered through blade (579) for cutting or other surgical/therapeutic purposes may be distinguished from energy for stimulating/exciting nervous tissue in a variety of ways. For example, energy for cutting may have a different phase in comparison to energy for excitation. In other versions, energy for cutting may be delivered in a particular series of pulses while energy for nerve stimulus may be delivered between the pulses of the cutting energy. In yet other versions, energy for cutting and excitation may be multiplexed during delivery. In versions where surgical instrument (500) is an ultrasonic surgical instrument and blade (579) is an ultrasonic blade, the energy for cutting is a mechanical oscillation movement while the energy for excitation is electrical current. It will be appreciated that other ways of distinguishing energy for cutting and energy for excitation will be apparent to one of ordinary skill in the art in view of the teachings herein.

As with sensor (42) described above, sensor (520) is operable to detect changes associated with excited nervous tissue and is integrated into clamp arm (584). Surgical instrument (500) also comprises a pad (580) in communication with clamp arm (584) operable to prevent direct communication of energy from blade (579) to clamp arm (584). As a result, it will be appreciated that energy detected by sensor (520) is a result of excitation of nervous tissue rather than by a direct transfer of energy from blade (579) to clamp arm (584). Furthermore, in some versions, sensor (520) may be tuned or configured to avoid false positives in response to surgical and/or therapeutic activations of blade (579). In addition or in the alternative, a control logic/algorithm in communication with sensor (520) may be configured to distinguish between excitations caused by surgical/therapeutic activations of blade (579) and excitations caused by a nerve stimulus current. In versions where clamp arm (584) is omitted, sensor (520) may be incorporated into blade (579) and/or some other part of surgical instruments (500) in numerous ways that will be apparent to those of ordinary skill in the art in view of the teachings herein.

In the exemplary version, sensor (520) is shaped like a blunt crescent. Sensor (520) is positioned on clamp arm (584) at or around the distal tip of clamp arm (584) such that sensor (520) protrudes past clamp arm (584). Thus, when blade (579) and clamp arm (584) clamp around tissue, sensor (520) protrudes into or around surrounding tissue. It will be understood that sensor (520) may have any suitable shape. For example, in some versions, sensor (520) may cover clamp arm (584) entirely. In yet other exemplary versions, sensor (520) may comprise multiple sensors (520) spaced apart along clamp arm (584). Other suitable variations will be apparent to one of ordinary skill in the art in view of the teachings herein.

It will be appreciated that in some versions, sensor (520) may require electrical energy to function properly. Such energy may be delivered in some instances based on the opening and closing of clamp arm (584) in relation to blade (579). A joint (513) that joins clamp arm (584) and blade (579) may be integrated with a joint switch (515) such that once clamp arm (584) opens and reaches a certain angle in relation to blade (579), joint switch (515) triggers delivery of power to sensor (520) such that sensor (520) can then detect excited nervous tissue. In some versions, joint (513) may comprise a feedback mechanism, such as a detent, such that the user receives haptic feedback that clamp arm (584) has opened widely enough to trigger operation of sensor (520). The haptic feedback may include a click or vibration pulse, or any other suitable feedback. In some instances, rather than haptic feedback, surgical instrument (500) may illuminate a light such as an LED or output an audible cue. In yet other variations, no feedback may be provided at all, and sensor (520) may simply be activated without informing the user. In some instances, the actual activation of sensor may be delayed slightly for a duration of approximately 2 seconds. It will be appreciated that any suitable delay may be incorporated between the triggering of joint switch (515) and operation of sensor (520) to provide the user sufficient notice that sensor (520) will be activated. Additionally, in some versions, turning off sensor (520) may be achieved by closing clamp arm (584) and blade (579) past a certain angle or simply by opening clamp arm (584) in relation to blade (579) a second time in such a way that triggers joint switch (515) a second time. As sensor (520) turns off, surgical instrument (500) may provide the user with feedback (mechanical, visual, and/or audio, etc.) to inform the user that sensor (520) has been turned off.

As discussed above, sensor (520) may be operable to detect excited nervous tissue. As a result, as blade (579) provides excitation of nervous tissue, sensor (520) then detects those excitations allowing a user to determine whether to avoid or otherwise respond to the presence/proximity of such nervous tissue. Sensor (520) is also in communication with an indicator (522) such that indicator (522) is activated when sensor (520) detects nervous tissue. A user will thus be able to monitor indicator (522) as the user uses surgical instrument (500) to determine whether nervous tissue is nearby or has come into contact with clamp arm (584). As with other components, indicator (522) is merely optional. For instance, a surgeon may simply rely on visual observation of tissue twitching to detect excitation of nervous tissue. In other versions, the user may use an endoscope to view any twitching of nervous tissue. Other suitable imaging or visual aids may be used as would be apparent to one of ordinary skill in the art in view of the teachings herein.

Figure 5A:
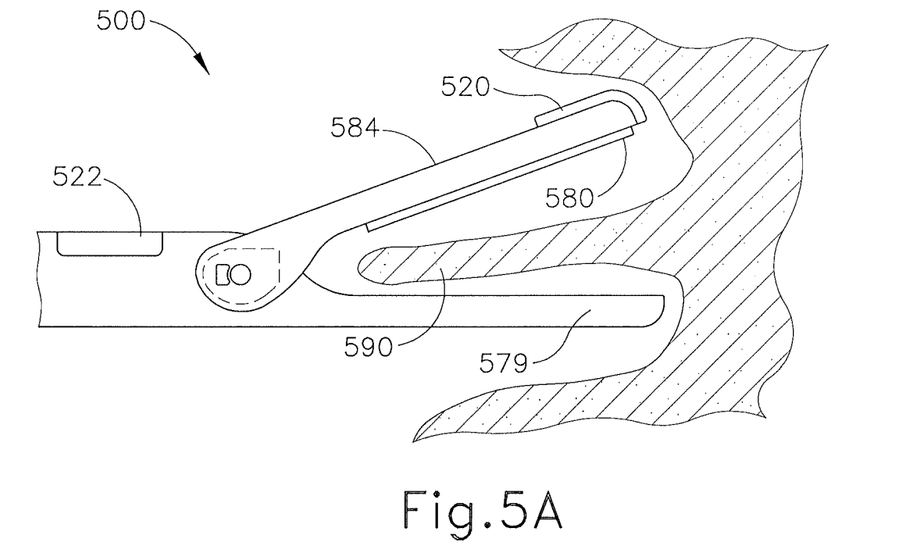
FIG. 5A depicts a side view of the end effector of FIG. 4 approaching tissue.
Figure 5B:
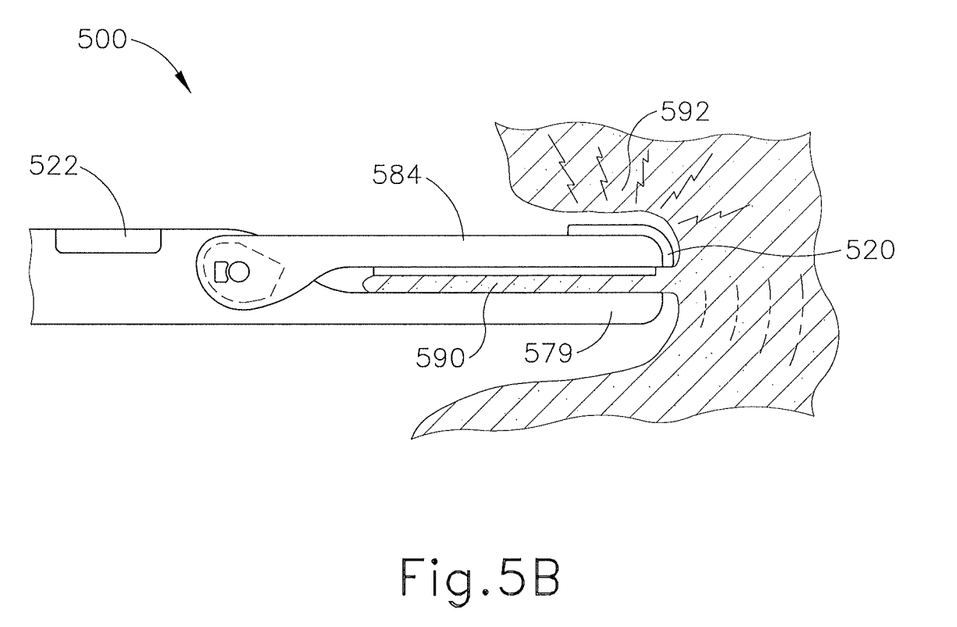
FIG. 5B depicts a side view of the end effector of FIG. 4 clamped on tissue and exciting nervous tissue.

FIGS. 5A-5B show an exemplary use of surgical instrument (500) as applied to tissue (590). In the illustrated version, surgical instrument (500) is configured to deliver ultrasonic energy to tissue (590) via end effector (512). However, it will be appreciated that surgical instrument (500) may be selected to perform any suitable surgical procedure for which it may be desirable to determine the proximity of nervous tissue. FIG. 5A shows surgical instrument (500) as it approaches tissue (590) to cut. Clamp arm (584) is open in relation to ultrasonic blade (579). FIG. 5B shows clamp arm (584) closed toward blade (579) with tissue (590) clamped between clamp arm (584) and blade (579). Pad (580) is positioned between clamp arm (584) and tissue. Additionally, in FIG. 5B, ultrasonic cutting energy is transmitted to tissue (590) via blade (579), thereby cutting tissue (590). At or around the same time, electrical current is transmitted through blade (579) to stimulate/excite nervous tissue. As can be seen in the exemplary version, excitation of nerves near tissue (590) that has been cut by surgical instrument (500) may result in either twitching or otherwise measurable excitation of nervous tissue. Sensor (520) is able to detect such nervous tissue excitation. Once sensor (520) detects excited nervous tissue (592), sensor (520) then triggers indicator (522), which may comprise a visual or audio signal to alert the user to know that nervous tissue is nearby. Thereafter, the user may react accordingly.

In some instances, sensor (520) may affect delivery of ultrasonic energy to blade (579) when sensor (520) detects excitation of nervous tissue (592). For instance, sensor (520) may be coupled with a logic in communication with the transducer activation circuit, and may at least temporarily cut electrical power to the transducer when sensor (520) detects excitation of nervous tissue (592), thereby rendering blade (579) inactive before blade (579) cuts the nervous tissue (592). In some such versions, the system may require the surgeon to reposition the end effector then release and re-actuate a trigger button or lever in order to re-activate the ultrasonic transducer. Similarly, before blade (579) is activated with ultrasonic energy (e.g., at the beginning of a surgical procedure), a control logic may drive the nerve stimulus feature and check feedback from sensor (520), and prevent blade (579) from being activated unless sensor (520) fails to indicate the presence/proximity of nervous tissue. In addition or in the alternative, the system may provide a surgeon override feature enabling the surgeon to selectively continue activation of the ultrasonic transducer despite the proximity of blade (579) to nervous tissue. In addition or in the alternative to affecting activation of the ultrasonic transducer, sensor (520) may trigger delivery of a therapeutic substance or other type of substance via the end effector of surgical instrument (500) when sensor (520) detects excitation of nervous tissue (592). Either or both of these functionalities, among others that will be apparent to those of ordinary skill in the art in view of the teachings herein, may be provided in addition to or in lieu of triggering indicator (522).

It should also be understood that responses triggered by sensor (520) may vary based on the level of nervous tissue excitation detected by sensor (520). For instance, a small degree of excitation detected by sensor (520) may simply result in triggering of indicator (522) to warn the surgeon that they are starting to approach nervous tissue; while a large degree of excitation detected by sensor (520) may result in at least temporary cutoff of electrical power to the ultrasonic transducer.

Similarly, indicator (522) may itself react differently based on levels of nervous tissue excitation detected by sensor (520) (e.g., flashing a yellow light and/or providing relatively infrequent audible tone pulses in response to a small degree of excitation; and flashing a red light and/or providing relatively rapid audible tone pulses in response to a large degree of excitation). Indicator (522) may also produce an audible signal to indicate surgical instrument (500) is in an "on" state and a further audible signal to indicate proximity of nervous tissue. For instance, indicator (522) may produce different tones such as a lower pitch tone indicating an "on" state and a higher pitch tone indicating contact with nervous tissue. As another merely illustrative example, indicator (522) may produce pulsed tones with a frequency indicative of proximity to nervous tissue. For instance, indicator (522) may produce periodic tones with a low frequency providing relatively long delay between the tones when nervous tissue is not in significant proximity to end effector (512); with an increasing frequency providing progressively shorter delay between the tones when end effector (512) approaches nervous tissue.

In some instances, surgical instrument (500) may be used to establish a nerve tissue map by the user. For example, sensor (520) may be operable to detect nervous tissue that is excited by surgical instrument (500), and a map may be generated based on feedback from sensor (520) and/or based on feedback from other instrument (500) components (e.g., accelerometers, etc.). In addition to nervous tissue detection, surgical instrument (500) may be operable to determine the spatial location of surgical instrument (500) such that detection of nervous tissue by sensor (520) may be associated with a spatial location. As the user detects nervous tissue by sensor (520) along several points in space, a map of the nervous tissue may be formed such that the user may more accurately be able to manipulate surgical instrument (500) in relation to such nervous tissue indicated by the nervous tissue map.

In some instances, surgical instrument (500) may produce heat that transfers to tissue, including nervous tissue, during normal use of surgical instrument (500). It may be desirable to determine if nervous tissue or nearby tissue conducts such heat. Sensor (520) may thus be operable to detect transferred heat directly through thermal detection or may be operable to detect changes in electrical properties of nervous tissue affected by heat (e.g., nervous tissue might exhibit a higher signal to noise alteration of evoked potential in response to heat). In some instances, once a certain threshold of heat has been detected, surgical instrument (500) may then notify the user.

Figure 6:
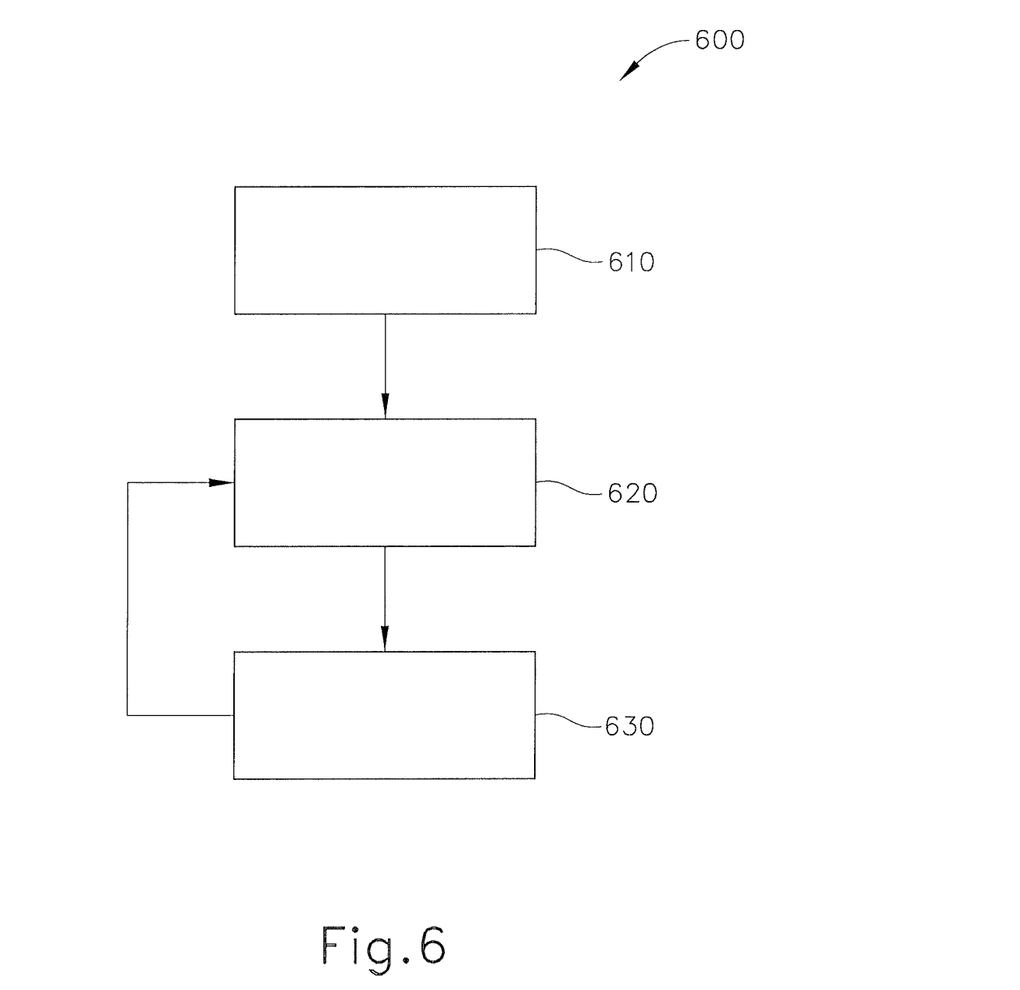
FIG. 6 depicts a flowchart view of an exemplary method of using a surgical instrument having the end effector of FIG. 4.

FIG. 6 shows an exemplary method (600) of using surgical instrument (500). As an initial step (610), the user may activate surgical instrument (500). In some cases, surgical device may be automatically activated as soon as power is supplied to the power source of surgical instrument (500), and in other versions, the user may select when to turn on surgical instrument (500). At or around the time where surgical instrument (500) is turned on by the user, user may insert surgical instrument (500) into the surgical site to be used in the surgical procedure.

Step (620) involves operating the surgical instrument (500). In the case of an ultrasonic surgical instrument (500), surgical instrument (500) may deliver ultrasonic vibrations through blade (579) to the surgical site. Such vibrations may be produced by pulsing electrical power to a transducer of surgical instrument (500). In some versions, an activation pulse is delivered to the transducer with a frequency ranging from one pulse every 10 milliseconds to one pulse every 100 milliseconds. Of course, any other suitable pulse frequency may be used as will be apparent to those of ordinary skill in the art in view of the teachings herein. These activation pulses cause peizeoelectric elements in the transducer to convert the electrical power into mechanical oscillatory/vibrational power, resulting in ultrasonic oscillations that are communicated along an acoustic waveguide to the ultrasonic blade (579). Between the electrical activation pulses delivered to the transducer to produce ultrasonic vibrations, surgical instrument (500) also delivers electrical current for the detection of nervous tissue. Such stimulus current may also be delivered through the transducer, waveguide, and blade (579), without compromising the acoustic performance of these components. For instance, the parameters of the nerve stimulus electrical current may be selected to not excite the piezoelectric elements in the transducer. Some versions of surgical instrument (500) may be operable to deliver nerve stimulus electrical current at the same time as transducer activation pulses. For instance, the electrical path for the nerve stimulus electrical current may be completely separate and isolated relative to the electrical path for activation of the transducer. Other variations for providing electrical current for nervous tissue detection and ultrasonic transducer activation will be apparent to one of ordinary skill in the art in view of the teachings herein.

In some instances, during the step (620) of operating surgical instrument (500), ultrasonic vibrations provided by surgical instrument (500) may be used to provide pressure to nervous tissue, thereby resulting in detectable changes to nervous tissue as the nervous tissue is excited, which allows the user to locate the nervous tissue. For example, an amplitude modulated resonant excitation signal may be produced by an ultrasonic transducer of surgical instrument (500) to excite nervous tissue. As another merely illustrative example, a frequency modulated resonant signal or a pulse width modulated resonant frequency may be produced that alternates in the time domain with the resonant frequency. In yet other instances, end effector (512) of surgical instrument (500) may be shaped such that during usage of surgical instrument in step (620), cavitational pressure may be generated around nervous tissue that excites or otherwise produces a measurable change in nervous tissue. In yet other versions, a separate acoustic driver could be used in step (620) during use of surgical instrument (500), which may be operable to create an acoustic wave in nervous tissue, thereby exciting it in a measurable manner.

The user in step (630) simply observes the site to determine whether excitation of nervous tissue has occurred. It will be appreciated that at least in some instances, nervous tissue will twitch and/or become visibly excited in a manner proportional to the closeness and strength of the energy being delivered to the nervous tissue. Energy for detecting nervous tissue may be continually delivered by returning to step (620), which thereby allows a user to continually monitor whether nervous tissue is nearby or otherwise in danger of being harmed. In some instances, the user may survey a surgical area by using surgical instrument (500) prior to activating blade (579) for surgical and/or therapeutic purposes. By doing so, the user can observe nervous tissue response and determine what areas of a surgical site contain nervous tissue before cutting tissue. The surgeon may still nevertheless wish to continue the stimulus and monitoring throughout the surgical procedure, even if the surgeon had performed a stimulus survey of the surgical site before activating blade (579) for surgical and/or therapeutic purposes.

During step (630), it will be understood that energy for exciting and subsequently detecting nervous tissue may be transmitted through blade (579) or through clamp arm (584) separately. In other versions, energy for exciting and detecting nervous tissue may be transmitted through both blade (579) and clamp arm (584) simultaneously. In yet other versions, energy for detecting nervous tissue may be transmitted through blade (579) while clamp arm (584) is omitted entirely. Other suitable variations will be apparent to one of ordinary skill in the art in view of the teachings herein.

While the exemplary version contemplates the user visually monitoring nervous tissue twitch, it will be appreciated that in some versions, an indicator may be used to signal the proximity of nervous tissue. Such an indicator may be constructed as discussed with respect to indicator (522) shown in FIGS. 5A-5B. It will further be contemplated that such an indicator may be operable to indicate the closeness of nervous tissue, by, for example, producing a brighter visual indicator or louder audio indicator as surgical instrument (500) moves closer to nervous tissue.

In some versions, it will be appreciated that surgical instrument (500) may be used in a patient having other medical devices including implants, fasteners, or other instruments at or near the surgical site. In those situations, it may be desirable to gauge proximity of surgical instrument (500) to such items. It will be appreciated that in some instances, such items may be metallic, plastic, or any other material providing a change in the electrical properties of the surrounding tissue. Accordingly, the electrical stimulus and sensing mechanisms of surgical instrument (500) may detect the proximity of those items. Other suitable uses for surgical instrument (500) will be apparent to one of ordinary skill in the art.

While examples above related to surgical instrument (10) in the form of an ultrasonic surgical instrument, it should be understood that the teachings herein may be readily applied to various types of electrosurgical instruments, including but not limited to those taught in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, issued as U.S. Pat. No. 9,161,803 on Oct. 20, 2015, the disclosure of which is incorporated by reference herein.

Furthermore, the teachings herein may be readily applied to various types of electrically powered cutting and stapling instruments, including but not limited to those taught in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pub. No. 2009/0209979, entitled "Motorized Cutting and Fastening Instrument Having Control Circuit for Optimizing Battery Usage," published Aug. 20, 2009, issued as U.S. Pat. No. 8,622,274 on Jan. 7, 2014; and U.S. patent application Ser. No. 13/151,481, entitled "Motor Driven Electrosurgical Device with Mechanical and Electrical Feedback," filed Jun. 2, 2011, issued as U.S. Pat. No. 9,161,803 on Oct. 20, 2015, the disclosure of which is incorporated by reference herein. Still other suitable types of devices to which the teachings herein may be applied will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery system is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector including an ultrasonic blade configured to deliver an ultrasonic energy to a surgical site, wherein the ultrasonic blade is further configured to deliver a nerve excitation energy to a nerve tissue at the surgical site; and
   (b) a control module operatively connected to the ultrasonic blade and configured to selectively activate the ultrasonic blade to deliver the ultrasonic energy to the surgical site, wherein the control module is configured to further activate the ultrasonic blade to deliver the nerve excitation energy to the nerve tissue thereby generating a biological response in the nerve tissue to the nerve excitation energy, and
   wherein the control module is further configured to receive the biological response from the nerve tissue and modify the delivery of ultrasonic energy to the surgical site based on the biological response; and
   (c) a sensor positioned on the end effector and operatively connected to the control module, wherein the sensor is configured to detect the biological response of the excitation of nerve tissue generated by the nerve excitation energy for communication to the control module, and
   wherein at least one of the control module or the sensor is configured to distinguish the biological response in the nerve tissue to the nerve excitation energy from another biological response in the nerve tissue to the ultrasonic energy.

2. The surgical instrument of claim 1, wherein the sensor distally protrudes beyond the ultrasonic blade.

3. The surgical instrument of claim 1, wherein the end effector further includes a clamp arm configured to selectively pivot toward and away from the ultrasonic blade, wherein the sensor is positioned on the clamp arm.

4. The surgical instrument of claim 3, wherein the sensor is positioned on a distal end portion of the clamp arm.

5. The surgical instrument of claim 3, further comprising a pad positioned on the clamp arm, wherein the pad is configured to prevent direct communication of the ultrasonic energy from the ultrasonic blade to the sensor.

6. The surgical instrument of claim 3, further comprising a joint switch operatively connected to the clamp arm and the ultrasonic blade and configured to trigger delivery of power to the sensor when the clamp arm is in a certain angle in relation to ultrasonic blade for detecting the biological response.

7. The surgical instrument of claim 1, wherein the control module is further configured to modify the delivery of ultrasonic energy to the surgical site based on the biological response by terminating delivery of the ultrasonic energy via the ultrasonic blade when the control module receives the biological response from the nerve tissue.

8. The surgical instrument of claim 7, wherein the control module is further configured to modify the delivery of ultrasonic energy to the surgical site based on the biological response by preventing delivery of the ultrasonic energy via the ultrasonic blade unless the control module fails to receive the biological response from the nerve tissue.

9. The surgical instrument of claim 7, wherein the biological response from the nerve tissue includes a small degree of nerve excitation and a large degree of nerve excitation, wherein the control module is configured to communicate to a user when the control module receives the small degree of nerve excitation while delivering ultrasonic energy via the ultrasonic blade to the surgical site, and wherein the control module is configured to terminate delivery of the ultrasonic energy via the ultrasonic blade when the control module receives the large degree of nerve excitation.

10. The surgical instrument of claim 1, further comprising an indicator operatively connected to the control module, wherein the indicator is configured to indicate to a user when the control module receives the biological response from the nerve tissue.

11. A surgical instrument, comprising:
    (a) an end effector including an ultrasonic blade configured to deliver an ultrasonic energy to a surgical site, wherein the end effector is configured to deliver a nerve excitation energy to a nerve tissue at the surgical site;
    (b) a sensor positioned on the end effector and configured to detect a biological response in the nerve tissue from the nerve excitation energy; and
    (c) a control module operatively connected to the ultrasonic blade and the sensor, wherein the control module is configured to selectively activate the ultrasonic blade to deliver the ultrasonic energy to the surgical site, wherein the control module is configured to further activate the end effector to deliver the nerve excitation energy to the nerve tissue thereby generating the biological response in the nerve tissue to the nerve excitation energy, and
    wherein the control module is further configured to receive the detected biological response of the nerve tissue from the sensor and modify the delivery of ultrasonic energy to the surgical site based on the biological response, and
    wherein at least one of the sensor or the control module is configured to distinguish the biological response in the nerve tissue to the nerve excitation energy from another biological response in the nerve tissue to the ultrasonic energy.

12. The surgical instrument of claim 11, wherein the sensor distally protrudes beyond the ultrasonic blade.

13. The surgical instrument of claim 11, wherein the end effector further includes a clamp arm configured to selectively pivot toward and away from the ultrasonic blade, wherein the sensor is positioned on the clamp arm.

14. The surgical instrument of claim 11, further comprising a pad positioned on the end effector, wherein the pad is configured to prevent direct communication of the ultrasonic energy from the ultrasonic blade to the sensor.

15. A surgical instrument, comprising:
(a) an end effector including an ultrasonic blade configured to deliver an ultrasonic energy to a surgical site thereby generating a first biological response in a nerve tissue at the surgical site, wherein the end effector is further configured to deliver a nerve excitation energy to the surgical site thereby generating a second biological response in the nerve tissue at the surgical site; and
(b) a control module operatively connected to the ultrasonic blade and configured to selectively activate the ultrasonic blade to deliver the ultrasonic energy to the surgical site, wherein the control module is configured to further activate the end effector to deliver the nerve excitation energy to the nerve tissue thereby generating the second biological response in the nerve tissue, and
wherein the control module is further configured to receive the second biological response from the nerve tissue and modify the delivery of ultrasonic energy to the surgical site based on the second biological response, and
wherein at least one of the end effector or the control module is configured to distinguish the second biological response in the nerve tissue to the nerve excitation energy from the first biological response in the nerve tissue to the ultrasonic energy.

* * * * *